United States Patent [19]

Haga et al.

[11] Patent Number: 4,831,149
[45] Date of Patent: May 16, 1989

[54] INDAZOLE COMPOUNDS, AND THEIR PRODUCTION AND USE

[75] Inventors: Toru Haga, Takarazuka; Eiki Nagano, Nishinomiya; Kouichi Morita; Ryo Sato, both of Toyonaka, all of Japan

[73] Assignee: Sumitomo Chemical Company, Limited, Osaka, Japan

[21] Appl. No.: 204,018

[22] Filed: Jun. 8, 1988

Related U.S. Application Data

[62] Division of Ser. No. 8,314, Jan. 29, 1987.

[30] Foreign Application Priority Data

| Jan. 29, 1986 | [JP] | Japan | 61-19044 |
| Apr. 7, 1986 | [JP] | Japan | 61-79661 |
| Apr. 7, 1986 | [JP] | Japan | 61-79662 |
| Apr. 7, 1986 | [JP] | Japan | 61-79663 |
| Apr. 9, 1986 | [JP] | Japan | 61-81420 |
| Apr. 9, 1986 | [JP] | Japan | 61-81421 |

[51] Int. Cl.$^4$ .................................... C07D 231/56
[52] U.S. Cl. ............................. 548/159; 548/357; 548/369

[58] Field of Search .................. 548/159, 359, 369

[56] References Cited

U.S. PATENT DOCUMENTS 4,670,043 6/1987 Nagano ................. 71/92
4,720,297 1/1988 Haga ..................... 71/90

Primary Examiner—Robert Gerstl
Attorney, Agent, or Firm—Birch, Stewart, Kolasch & Birch

[57] ABSTRACT

A compound of the formula:

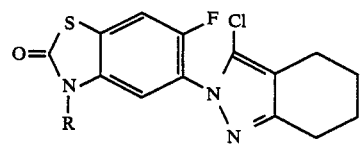

wherein R is a $C_1$–$C_5$ alkyl group, a $C_3$–$C_4$ alkenyl group, a $C_3$–$C_4$ alkynyl group or a $C_1$–$C_3$ alkoxy($C_1$–$C_2$)alkyl group, which is useful as a herbicide.

1 Claim, No Drawings

INDAZOLE COMPOUNDS, AND THEIR PRODUCTION AND USE

This application is a divisional of copending application Ser. No. 008,314, filed on Jan. 29, 1987.

The present invention relates to indazole compounds, and their production and use. More particularly, it relates to novel indazole compounds, a process for producing them, and their use as herbicides.

Some tetrahydro-2H-indazole derivatives are known to be effective as herbicides (U.S. Pat. No. 4,059,434). However, their herbicidal activity is not sufficiently high. Further, their selectivity between crop plants and undesired weeds is inferior. Thus, they are not always satisfactory for current use.

It has now been found that the indazole compounds of the formula:

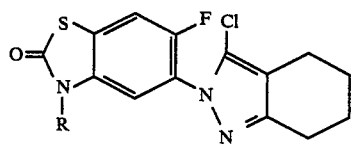
(I)

wherein R is a $C_1$–$C_5$ alkyl group, a $C_3$–$C_4$ alkenyl group, a $C_3$–$C_4$ alkynyl group or a $C_1$–$C_3$ alkoxy($C_1$–$C_2$)alkyl group show a high herbicidal activity against a wide variety of weeds including broad-leaved weeds, Graminaceous weeds, Commelinaceous weeds and Cyperaceous weeds in agricultural plowed field by foliar or soil treatment without producing any material phytotoxicity on various agricultural crops such as corn, sorghum, wheat, barley, rice plant, soybean, peanut and cotton. Examples of the broad-leaved weeds are wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), tall morningglory (*Ipomoea purpurea*), field bindweed (*Convolvulus arvensis*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), sun spurge (*Euphorbia helioscopia*), etc. Examples of Graminaceous weeds are Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), etc. Examples of Commelinaceous weeds are asiatic dayflower (*Commelina communis*), etc. Examples of the Cyperaceous weeds are rice flatsedge (*Cyperus iria*), yellow nutsedge (*Cyperus esculentus*) etc.

It is especially notable that some of the indazole compounds (I) exert a prominent herbicidal activity by soil application before or after germination of undesired weeds in the paddy field without any material phytotoxicity. For instance, they show a high herbicidal potency on broad-leaved weeds such as common falsepimpernel (*Lindernia procumbens*), indian toothcup (*Rotala indica*) and waterwort (*Elatine triandra*), Graminaceous weeds such as barnyardgrass (*Echinochloa oryzicola*), Cyperaceous weeds such as Sm.fl. umbrella sedge (*Cyperus difformis*), hardstem bulrush (*Scirpur juncoides*) and needle spikerush (*Eleocharis acicularis*) and others such as monochoria (*Monochoria vaginalis*) and arrowhead (*Sagittaria pygmaea*) without producing any material phytotoxicity to rice plants on flooding treatment.

Among the indazole compounds (I), preferred are those wherein R is a $C_2$–$C_4$ alkyl group, a $C_3$–$C_4$ alkenyl group, a $C_3$–$C_4$ alkynyl group or a $C_1$–$C_3$ alkoxymethyl group. The most preferred are 3-chloro-2-[6-fluoro-3-(2-propynyl)2H-benzothiazolon-5-yl]-4,5,6,7-tetrahydro-2H-indazole, 3-chloro-2-(6-fluoro-3-isopropyl-2H-benzothiazolon-5-yl)-4,5,6,7-tetrahydro-2H-indazole, etc.

The indazole compound (I) is obtainable by reacting 3-chloro-2-[6-fluoro-2(3H)-benzothiazolon-5-yl]-4,5,6,7-tetrahydro-2H-indazole of the formula:

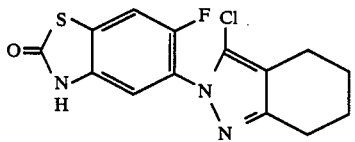
(II)

with an R-introducing agent of the formula:

R—X  (III)

wherein X is a leaving group such as a halogen atom (e.g. chlorine, bromine or iodine) and R is as defined above.

The reaction is usually carried out in an inert solvent in the presence of an acid eliminating agent at a temperature of 0° to 80° C. for a period of 1 to 24 hours. The amounts of the R-introducing agent (III) and the acid eliminating agent may be respectively 1 to 3 equivalents and 1 to 3 equivalents to one equivalent of the starting compound (II).

Examples of the inert solvent include aromatic hydrocarbons (e.g. benzene, toluene, xylene), nitriles (e.g. acetonitrile, isobutylonitrile), acid amides (e.g. formamide, N,N-dimethylformamide, N,N-dimethylacetamide), dimethylsulfoxide, water, and a mixture thereof. As the acid eliminating agent, there may be exemplified an inorganic base (e.g. sodium hydroxide, potassium hydroxide, potassium carbonate, sodium hydride), etc.

After completion of the reaction, the reaction mixture is subjected to ordinary post-treatment such as dilution with water, extraction with an organic solvent and concentration. If desired, any conventional purification procedure such as chromatography and recrystallization may be adopted.

The indazole compound (I) is also obtainable by reacting a hexahydroindazolone compound of the formula:

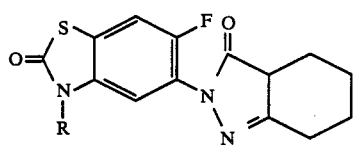

(IV)

wherein R is as defined above (available in a tautomeric mixture form) with a chlorinating agent.

The reaction is usually accomplished in an inert solvent at a temperature of 60° to 200° C., preferably of 100° to 180° C., under a normal pressure or an elevated pressure. The chlorinating agent may be used in an amount of 1 to 4 equivalents to one equivalent of the starting compound (IV).

Examples of the chlorinating agent are phosgene, trichloromethyl chloroformate, oxalyl chloride, etc. As the inert solvent, there may be exemplified aromatic hydrocarbons (e.g. chlorobenzene, toluene, xylene), halogenated hydrocarbons (e.g. 1,2-dichloroethane, 1,1,1-trichloroethane), etc.

After completion of the reaction, excess of the chlorinating agent as well as the solvent are removed. If desired, the residue may be purified by chromatography or recrystallization.

Typical examples of the indaole compounds (I) which can be produced by the above procedures are shown in Table 1.

TABLE 1

(I)

| R |
|---|
| CH$_3$ |
| C$_2$H$_5$ |
| n-C$_3$H$_7$ |
| i-C$_3$H$_7$ |
| n-C$_4$H$_9$ |
| i-C$_4$H$_9$ |
| sec-C$_4$H$_9$ |
| sec-C$_5$H$_{11}$ |
| n-C$_5$H$_{11}$ |
| i-C$_5$H$_{11}$ |
| CH$_2$=CHCH$_2$— |
| CH$_3$CH=CHCH$_2$— |
| CH≡CCH$_2$— |
| CH$_3$C≡CCH$_2$— |
| CH$_3$OCH$_2$— |
| C$_2$H$_5$OCH$_2$— |
| n-C$_3$H$_7$OCH$_2$— |

Practical and presently preferred embodiments for production of the indazole compounds (I) are illustratively shown in the following examples.

EXAMPLE 1

A suspension of sodium hydride (60 % oil; 50 mg) in N,N-dimethylformamide (3 ml) was cooled to 0° C., and 3-chloro-2-(6-fluoro-2(3H)-benzothiazolon-5-yl)-4,5,6,7-tetrahydro-2H-indazole (390 mg) was added thereto at 0° C., followed by stirring at the same temperature for 30 minutes. To the suspension, propargyl bromide (160 mg) was added, and the resultant mixture was heated to a temperature of 50° to 60° C. and allowed to react at the same temperature for 2 to 3 hours. Water was added to the reaction mixture, which was extracted with ethyl acetate. The extract was washed with water, dried and concentrated. The residue was purified by silica gel thin layer chromatography using a mixture of ethyl acetate and hexane (1 : 4) as a developing solvent to give 3-chloro-2-[6-fluoro-3-(2-propynyl)-2H-benzothiazolon5-yl]-4,5,6,7-tetrahydro-2H-indazole (24.1 mg). m.p., 130°–132° C.

EXAMPLE 2

2-(6-Fluoro-3-sec-butylbenzothiazolon-5-yl)3,3',4,5,6,7-hexahydro-2H-indazol-3-one (9.37 g), toluene (20 ml), 1,2-dichloroethane (30 ml) and trichloromethylchloroformate (5.2 ml) were charged in an autoclave made of Harstelloy, and the resultant mixture was allowed to react at a temperature of 120° to 130° C. for 3 hours under pressure. After cooling, the reaction mixture was concentrated under reduced pressure, and the residue was purified by silica gel column chromatography using a mixture of hexane and ethyl acetate as an eluent to give 3-chloro-2-(6-fluoro-3-sec-butyl2H-benzothiazolon-5-yl)-4,5,6,7-tetrahydro-2H-indazole (3.88 g). n$_D^{22.5}$ 1.5713.

In the same manner as above, the indazole compounds (I) as shown in Table 2 were obtained.

TABLE 2

(I)

| Compound No. | R | Physical property |
|---|---|---|
| 1 | C$_2$H$_5$ | resinous |
| 2 | n-C$_3$H$_7$ | n$_D^{25.0}$ 1.5908 |
| 3 | CH$_2$=CHCH$_2$— | resinous |
| 4 | CH≡CCH$_2$— | m.p. 130–132° C. |
| 5 | CH$_3$OCH$_2$— | m.p. 141–142° C. |
| 6 | iso-C$_3$H$_7$ | resinous |
| 7 | sec-C$_4$H$_9$ | n$_D^{22.5}$ 1.5713 |
| 8 | (C$_2$H$_5$)$_2$CH— | n$_D^{23.5}$ 1.5763 |

The starting compounds (II) and (IV) can be produced respectively according to Routes (A) and (B) as shown below:

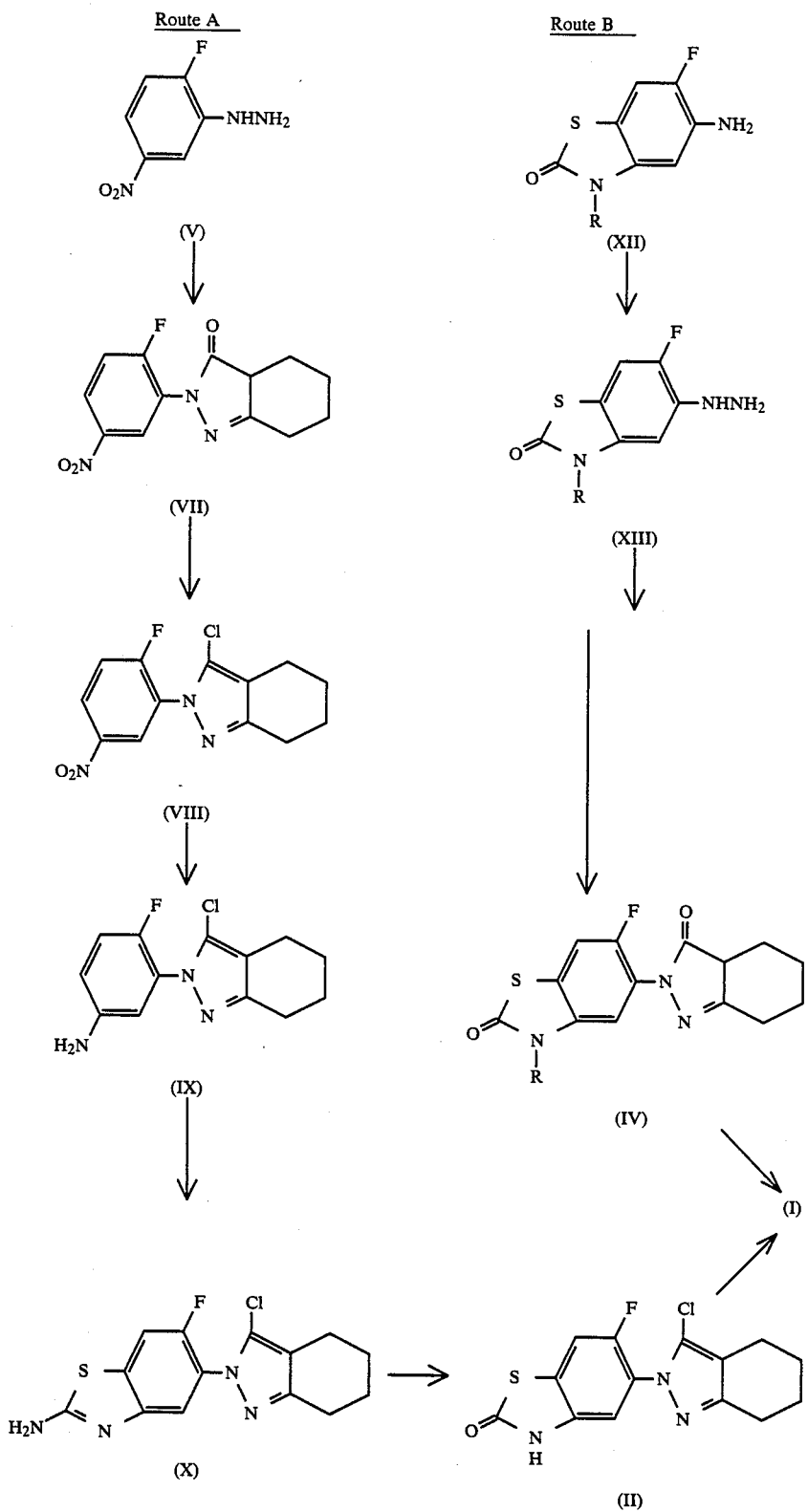
wherein R is as defined above.
Route A
Step (1):
2-Fluoro-5-nitrophenylhydrazine (V) is reacted with a 2-cyclohexanonecarboxylic ester of the formula:

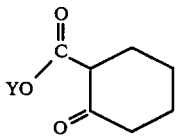

wherein Y is $C_1$-$C_8$ alkyl to give 2-(2-fluoro-5-nitrophenyl)-1,2,4,5,6,7-hexahydro-3H-indazole (in a tautomeric mixture form) (VII).

The reaction is accomplished at a temperature of 20° to 120° C. for a period of 1 to 24 hours in an inert solvent such as a lower aliphatic carboxylic acid (e.g. acetic acid, propionic acid). The compound (VI) may be used in an amount of 1 to 1.5 equivalents to the compound (V).

After completion of the reaction, the reaction mixture is poured into ice-water, and the precipitated crystals are collected by filtration. If necessary, any conventional purification procedure such as recrystallization or chromatography may be applied.

The starting compound (V) can be produced from 2-fluoro-5-nitroaniline by the method as described in [J.Chem.Soc., (C), 1970, 2106].

Step (2)

2-(2-Fluoro-5-nitrophenyl)-1,2,4,5,6,7-hexahydro-3H-indazole (VII) is reacted with a chlorinating agent, if necessary, in the presence of a dehydrohalogenating agent to give 3-chloro-2-(2-fluoro-5-nitrophenyl)-4,5,6,7-tetrahydro-2H-indazole (VIII).

The reaction is carried out in an inert solvent at a temperature of 20° to 200° C., preferably of 80° to 130° C., under a pressure of normal pressure to 50 kg/cm² for a period of 1 to 240 hours. As the chlorinating agent, there are exemplified phosgene, oxalyl chloride, trichloromethyl chloroformate, phosphorus oxychloride, thionyl chloride, etc. Examples of the dehydrochlorinating agent are an organic base (e.g. pyridine, triethylamine, N,N-diethylaniline), etc. Further, the chlorinating gent and the dehydrochlorinating agent may be respectively used in amounts of 1 to 15 equivalents and of a catalytic amount to 1 equivalent to one equivalent of the compound (VII).

As the solvent, there may be employed, for instance, aliphatic hydrocarbons (e.g. hexane, ligroin), aromatic hydrocarbons (e.g. toluene, benzene, xylene), halogenated hydrocarbons (e.g. chloroform, carbon tetrachloride, dichloroethane, tetrachloroethane, chlorobenzene, dichlorobenzene), ethers (e.g. diisopropyl ether, dioxane, ethylene glycol dimethyl ether), tertiary amines (e.g. pyridine, triethylamine, N,N-dimethylmorpholine), or their mixtures.

After completion of the reaction, the reaction mixture is subjected to ordinary post-treatment such as concentration. If necessary, any conventional purification procedure such as recrystallization or chromatography may be applied.

Step (3):

3-Chloro-2-(2-fluoro-5-nitrophenyl)-4,5,6,7-tetrahydro-2H-indazole (VIII) is reacted with a reducing agent to give 2-(5amino-2-fluorophenyl)-3-chloro-4,5,6,7-tetrahydro2H-indazole (IX).

The reaction is usually carried out by treatment of the compound (VIII) with a reducing agent in an inert solvent at a temperature of 60° to 120° C. for a period of 1 to 24 hours.

As the reducing agent, there may be used iron powder, zinc powder, tin powder, ferrous chloride, zinc chloride, stannous chloride, etc. Examples of the inert solvent are aqueous solutions of acetic acid, hydrochloric acid, sulfuric acid, etc. If necessary, any organic solvent such as ethyl acetate may be present in the reaction system. The amount of the reducing agent is usually from 3 to 30 equivalents, preferably from 5 to 20 equivalents, to one equivalent of the compound (VIII).

After completion of the reaction, the residue is removed by filtration, and the filtrate is extracted with an organic solvent. The extract is washed with water or an aqueous solution of sodium bicarbonate and subjected to concentration. When desired, any conventional purification method, e.g. recrystallization or chromatography, may be also applied.

Step (4):

2-(5-Amino-2-fluorophenyl)-3-chloro-4,5,6,7-tetrahydro-2H-indazole (IX) is reacted with a thiocyanate and then with a halogen to give 2-(2-amino-6-fluorobenzothiazol-5-yl)-3-chloro-4,5,6,7-tetrahydro-2H-indazole (X).

The reaction is normally carried out in an inert solvent at a temperature of 0° to 50° C. for a period of 1 to 100 hours.

Examples of the thiocyanate are sodum thiocyanate, potassium thiocyanate, ammonium thiocyanate, etc. As the halogen, there may be used bromine, chlorine, etc. The inert solvent is, for instance, aqueous acetic acid, aqueous hydrochloric acid, aqueous sulfuric acid, etc. Usually, the thiocyanate and the halogen are respectively used in 1 to 10 equivalents and 1 to 10 equivalents to one equivalent of the compound (IX).

After completion of the reaction, the reaction mixture is neutralized and the precipitated crystals are collected by filtration and air-dried. If necessary, any conventional purification method such as recrystallization and chromatography may be applied.

Step (5):

2-(2-Amino-6-fluorobenzothiazol-5-yl)-3-chloro-4,5,6,7-tetrahydro-2H-indazole (X) is subjected to diazotiation, followed by decomposition of the resulting diazonium salt to give 3-chloro-2-[6-fluoro-2(3H)-benzpthiazolon-5-yl]-4,5,6,7-tetrahydro-2H-indazole (II).

The diazotiation is carried out by reacting the compound (X) with a diazotiating agent ordinarily in an inert solvent (e.g. aqueous sulfuric acid, aqueous hydrochloric acid) at a temperature of $-5°$ to 5° C. for a period of 0.5 to 24 hours, and the decomposition of the resulting diazonium salt is effected normally by heating at a temperature of 70° to 100° C. for a period of 0.5 to 24 hours. As the diazotiating agent, there may be employed an alkali metal nitrite such as sodium nitrite or potassium nitrite. The amount of the diazotiating agent is usually from 1 to 2 equivalents to the compound (X).

After completion of the reaction, the reaction mixture is diluted with water and extracted with an organic solvent, followed by conventional post-treatment such as washing with water, drying and concentration. If necessary, any purification method such as chromatography may be applied.

The compounds (VII), (VIII), (IX) and (X) as produced in the above Route A are novel and can be covered by the general formula:

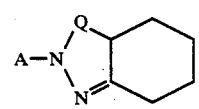

(XI)

wherein A is

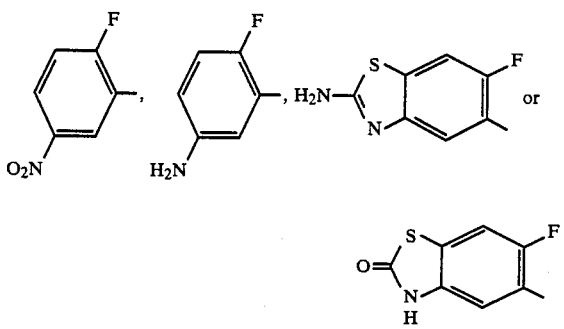

and Q is —C(=O)— or —C(Cl)= but when Q is —C(=O), A is

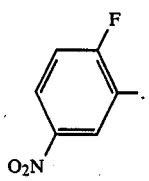

Practical examples of the conversions in the above Route (A) are illustratively shown below.

EXAMPLE 3

A solution of 2-fluoro-5-nitrophenylhydrazine (53.95 g) in ethyl 2-cyclohexanonecarboxylate (53.65 g) was heated under reflux for 4 hours. After cooling, the reaction mixture was poured into ice-water. The precipitated crystals were collected by filtration, washed with water and hexane and dried to obtain 2-(2-fluoro-5-nitrophenyl)1,2,4,5,6,7-hexahydro-3H-indazol-3-one. m.p., 220.0° C.

EXAMPLE 4

To a solution of 2-(2-fluoro-5-nitrophenyl)1,2,4,5,6,7-hexahydro-3H-indazol-3-one (66.87 g) in toluene (125 ml) and 1,2-dichloroethane (175 ml), there was added trichloromethyl chloroformate (71.57 g), and the resultant mixture was allowed to react in an autoclave at a temperature of 120° to 130° C. under a pressure of 25 kg/cm$^2$, for 3 hours. After cooling, the solvent was removed by distillation. The residue was purified by silica gel column chromatography using a mixture of ethyl acetate and n-hexane (1 : 6) as an eluent to give 3-chloro-2-(2-fluoro-5-nitrophenyl)-4,5,6,7-tetrahydro-2H-indazole. m.p., 109.1° C.

EXAMPLE 5

To a suspension of iron powder (28.75 g) in 5 % aqueous acetic acid (57.5 ml) heated at 80° C., a solution of 3-chloro-2-(2-fluoro-5-nitrophenyl)-4,5,6,7-tetrahydro-2H-indazole (30.45 g) in acetic acid (103 ml) and ethyl acetate (103 ml) was aded, and the resultant mixture was heated at a temperature of 60° to 80° C. under reflux for 3 hours. After cooling, water and ethyl acetate were added to the reaction mixture. The residue was removed by filtration. The filtrate was extracted with ethyl acetate, and the extract was washed with water and an aqueous sodium bicarbonate solution, dried and concentrated to give 2-(5-amino-2-fluorophenyl)-3-chloro-4,5,6,7-tetrahydro-2H-indazole (22.97 g). m.p., 120.9° C.

EXAMPLE 6

2-(5-Amino-2-fluorophenyl)-3-chloro-4,5,6,7-tetrahydro-2H-indazole (22.97 g) was dissolved in 95 % aqueous acetic acid (79.53 g), and ammonium thiocyanate (15.92 g) was added thereto at room temperature (ca. 20° C). To the resultant mixture, a solution of bromine (15.89 g) in acetic acid (23.77 g) was dropwise added in 105 minutes. After being allowed to stand overnight, the mixture was heated to 100° C., and hot water (173 ml) was added thereto, followed by filtration. The filtrate was cooled and neutralized with sodium carbonate. The precipitated crystals were collected by filtration and dried to give 2-(2-amino-6-fluorobenzothiazol-5-yl)-3-chloro-4,5,6,7-tetrahydro-2H-indazole (8.77 g). m.p., 212.4° C.

EXAMPLE 7

A suspension of 3-chloro-2-(2-amino-6-fluorobenzothiazol-5-yl)-4,5,6,7-tetrahydro-2H-indazole (8.77 g) in 50% sulfuric acid (68 ml) was cooled to a temperature of 0° to 5° C., and a saturated aqueous solution of sodium nitrite (2.43 g) was dropwise added thereto at the same temperature, followed by stirring at the same temperature for 20 minutes. The diazonium salt solution thus obtained was dropwise added to a mixture of water (23 ml) and conc. sulfuric acid (34 ml) heated at 90° C. and allowed to react at 80° to 100° C. for 30 minunites. After cooling, the reaction mixture was combined with water and extracted with ethyl acetate, washed with water, dried and concentrated to give 3-chloro-2-[6-fluoro-2(3H)-benzothiazolon-5-yl]-4,5,6,7-tetrahydro-2H-indazole (0.39 g).

$^1$H NMR δ (CDCl$_3$): 1.5–2.1 (br, 4H), 2.2–3.0 (br, 4H), 6.0–6.9 (br, 1H), 7.19 (d, 1H, J=9.0 Hz), 7.20 (d, 1H, J=6.0 Hz).

Route B

Step (6)

The aminobenzothiazolone (XII) is diazotiated to the diazonium salt, and then the latter is reduced with stannous chloride to give the hydrazinobenzthiazolone (XIII).

For the diazotiation, the aminobenzothiazolone (XII) is reacted with an alkali metal nitrite (e.g. sodium nitrite, potassium nitrite) usually in an amount of 1 to 1.2 equivalents in the presence of large excess of an acid (e.g. hydrochloric acid, sulfuric acid) at a temperature of −5° to 0° C.

After removal of the remaining nitrite ion, the produced diazonium salt is reduced with stannous chloride in an amount of 3 to 5 equivalents at a temperature of −40° to 0° C. to give the hydrazinobenzthiazolone (XIII) in a salt form. Neutralization of the salt at a temperature below 10° C., followed by extraction with an organic solvent and concentration of the extract gives the hydrazinobenzthiazolone (XIII). When desired, the product may be purified by chromatography.

Step (7):

The hydrazinobenzthiazolone (XIII) is reacted with a cyclohexanonecarboxylic ester (VI) to give the hexahydroindazolone (in a tautomeric mixture form) (IV).

This reaction is carried out at a temperatrue of 20° to 120° C. in an inert solvent (e.g. acetic acid, propionic acid). The amount of the cyclohexanonecarboxylic ester (VI) is usually from 1 to 1.1 equivalents to the compound (XIII).

The reaction mixture is poured into water and subjected to ordinary post-treatment such as extraction with an organic solvent and concentration. If necessary, any purification procedure such as chromatography and recrystallization may be applied.

The compounds (XIII) and (IV) as produced in the above Route B are novel and can be covered by the general formula:

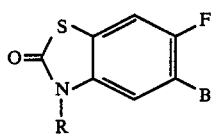

(XIV)

wherein B is —NHNH$_2$ or

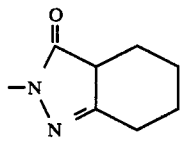

and R is as defined above.

Practical embodiments of the conversions in Route B are shown in the following Examples.

EXAMPLE 8

5-Amino-6-fluoro-3-sec-butylbenzothiazolone (22.95 g) was combiend with conc. hydrochloric acid (300 ml), and the resultant mixture was stirred at room temperature for 30 minutes. After cooling to a temperature of −5° to 5° C., a solution of sodium nitrite (6.89 g) in water (30 ml) was dropwise added thereto, followed by stirring for 30 minutes. The reaction mixture was cooled to −30° C., and a solution of stannous chloride (36.2 g) in hydrochloric acid (82 ml) was added thereto, followed by stirring at −10° to 0° C. for 2 hours. The insoluble material was collected by filtration, dissolved in water, neutralized and extracted with ethyl acetate. The extract was dried and concentrated to give 5-hydrozino-6-fluoro-3-sec-butylbenzothiazolone (13.19 g) as a glassy substance.

In the same manner as above, the compounds (XII) as shown in Table 3 were obtained.

TABLE 3

(XIII)

| R | Physical property |
|---|---|
| iso-C$_3$H$_7$ | m.p. 66° C. |
| —CH$_2$CH=CH$_2$ | m.p. 130° C. |
| —CH$_2$C≡CH | m.p. 163–164° C. |

EXAMPLE 9

A mixture of 5-hydrazino-6-fluoro-3-sec-butylbenzothiazolone (6 g) and 2-ethoxycarbonylcyclohexanone (4 g) in acetic acid (23.5 ml) was refluxed for 2.5 hours. After cooling, water was added to the reaction mixure, which was extracted with ethyl acetate, washed with water, dried and concentrated to give 2-(6-fluoro-3-sec-butylbenzo-thiazolon-5-yl)-3,3',4,5,6,7-hexahydro-2H-indazol-3-one (10.36 g). n$_D^{22.5}$1.5736.

In the same manner as above, the compounds (IV) as shown in Table 4 were obtained:

TABLE 4

(IV)

| R | Physical property |
|---|---|
| iso-C$_3$H$_7$ | glassy |
| —CH$_2$CH=CH$_2$ | m.p. 178–179° C. |
| —CH$_2$C≡CH | m.p. 237–237.5° C. |

On the practical usage of the indazole compounds (I), they may be applied in conventional preparation forms such as emulsifiable concentrates, wettable powders, suspensions and granules in combination with conventional solid or liquid carriers or diluents as well as surface active agents or auxiliary agents. The content of the indazole compounds (I) as the active ingredient in such preparation forms is usually within a range of 0.01 to 90 % by weight, preferably of 0.02 to 80 % by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts are by weight. The compound number of the active ingredient corresponds to the one in Table 2.

FORMULATION EXAMPLE 1

Fifty parts of Compound No. 4, 3 parts of calcium ligninsulfonate, 2 parts of sodium laurylsulfate and 45 parts of synthetic hydrous silica are well mixed while being powdered to obtain a wettable powder.

FORMULATION EXAMPLE 2

Five parts of Compound No. 2, 14 parts of polyoxyethylenestyrylphenyl ether, 6 parts of calcium dodecylbenzenesulfonate, 30 parts of xylene and 45 parts of cyclohexanone are well mixed to obtain an emulsifiable concentrate.

FORMULATION EXAMPLE 3

Two parts of Compound No. 5, 1 part of synthetic hydrous silica, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 4 is mixed with 3 parts of polyoxyethylenesorbitan monooleate, 3 parts of carboxymethyl cellulose and 69 parts of water and pulverized until the particle size of the mixture becomes less than 5 microns to obtain a suspension.

FORMULATION EXAMPLE 5

Five parts of Compound No. 3, 4 or 5, 14 parts of polyoxyethylenestyrylphenyl ether, 6 parts of calcium dodecylbenzenesulfonate, 30 parts of xylene and 45 parts of N,N-dimethylformamide are well mixed to obtain an emulsifiable concentrate.

The indazole compounds (I) thus formulated in any suitable formulation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the indazole compounds (I) over the top of the plants. It may also be applied directly to the weeds if care is taken to keep the chemical off the crop foliage.

The indazole compounds (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the indazole compounds (I) can be used as herbicides applicable to agricultural plowed field as well as paddy field. They are also useful as herbicides to be employed for orchard, pasture land, lawn, forest, non-agricultural field, etc.

The dosage rate of the indazole compounds (I) may vary on prevailing weather conditions, formulation used, prevailing season, mode of application, soil involved, crop and weed species, etc. Generally, however, the dosage rate is from 0.02 to 100 grams, preferably from 0.04 to 50 grams, of the active ingredient per are. The herbicidal composition of the invention formulated in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the indazole compounds (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compounds shown in Table 5 below were used for comparison.

TABLE 5

| Compound No. | Chemical structure | Remarks |
| --- | --- | --- |
| A | (structure: dichlorophenyl-methoxy-N-N-indazole with Cl substituent, cyclohexyl fused) | U.S. Pat. No. 4,059,434 |
| B | (structure: 2,4,6-trichlorophenyl-O-phenyl-NO$_2$) | Commercially available fungcide "chloronitrofen" |

TEST EXAMPLE 1

Cylindrical plastic pots (diameter, 10 cm; height, 10 cm) were filled with upland field soil, and the seeds of Japanese millet, oats, tall morningglory and velvetleaf were sowed therein and covered with soil. A designed amount of the test compound formulated in an emulsifiable concentrate according to Formulation Example 2 or 5 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 6.

TABLE 6

| | | Herbicidal activity | | | |
| --- | --- | --- | --- | --- | --- |
| Compound No. | Dosage (g/are) | Japanese millet | Oats | Tall morning-glory | Velvet-leaf |
| 1 | 40 | 5 | 5 | 5 | 5 |
| 2 | 40 | 5 | 5 | 5 | 5 |
| 3 | 40 | 5 | 5 | 5 | 5 |
| 4 | 40 | 5 | 5 | 5 | 5 |
| 5 | 40 | 5 | 5 | 5 | 5 |
| 6 | 40 | 5 | 5 | 5 | 5 |
| 7 | 40 | 5 | 5 | 5 | 5 |

TEST EXAMPLE 2

Cylindrical plastic pots (diameter, 10 cm; height, 10 cm) were filled with upland field soil, and the seeds of Japanese millet, oats, radish and velvetleaf were sowed therein and cultivated in a greenhouse for 10 days. A designed amount of the test compound formulated in an emulsifiable concentrate according to Formulation Example 2 or 5 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. The results are shown in Table 7.

TABLE 7

| Compound No. | Dosage (g/are) | Herbicidal activity | | | |
|---|---|---|---|---|---|
| | | Japanese millet | Oats | Radish | Velvetleaf |
| 1 | 20 | 5 | 5 | 5 | 5 |
| 2 | 20 | 5 | 5 | 5 | 5 |
| 3 | 20 | 5 | 5 | 5 | 5 |
| 4 | 20 | 5 | 5 | 5 | 5 |
| 5 | 20 | 5 | 5 | 5 | 5 |
| 6 | 20 | 5 | 5 | 5 | 5 |
| 7 | 20 | 5 | 5 | 5 | 5 |
| 8 | 20 | 5 | 5 | 5 | 5 |

TEST EXAMPLE 3

Cylindrical plastic pots (diameter, 8 cm,; height, 12 cm) were filled with paddy field soil, and the seeds of barnyardgrass (*Echinochloa oryzicola*), broad-leaved weeds (i.e. common falsepimpernel, indian toothcup, waterwort) and hardstem bulrush were sowed in 1 to 2 cm depth. Water was poured therein to make a flooded condition. Buds of arrowhead were sowed in 1 to 2 cm depth, and the test plants were grown in a greenhouse. Six days (at that time weeds began to germinate) thereafter, a designed amount of the test compound formulated in an emulsifiable concentrate according to Formulation Example 2 or 5 and diluted with water (5 ml) was applied to the pots by perfusion. The test plants were grown for further 20 days in the greenhouse, and the herbicidal activity was examined. The results are shown in Table 8.

TABLE 8

| Compound No. | Dosage (g/are) | Herbicidal activity | | | |
|---|---|---|---|---|---|
| | | Barnyardgrass | Broadleaved weed | Hardstem bulrush | Arrowhead |
| 1 | 2.5 | 5 | 5 | 5 | 5 |
| 2 | 2.5 | 5 | 5 | 5 | 5 |
| 3 | 2.5 | 5 | 5 | 5 | 5 |
| 4 | 2.5 | 5 | 5 | 5 | 5 |
| 5 | 2.5 | 5 | 5 | 5 | 5 |
| 6 | 2.5 | 5 | 5 | 5 | 5 |
| 7 | 2.5 | 5 | 5 | 4 | 5 |
| B | 2.5 | 2 | 3 | 1 | 0 |

TEST EXAMPLE 4

Vats (33 cm × 23 cm × 11 cm) were filled with upland field soil, and the seeds of soybean, corn, velvet-leaf, black nightshade, common lambsquarters and redroot pigweed were sowed therein to 1 to 2 cm depth. A designed amount of the test compound formulated in an emulsifiable concentrate according to Formulation Example 2 or 5 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 9.

TABLE 9

| Compound No. | Dosage (g/are) | Herbicidal activity | | | | | |
|---|---|---|---|---|---|---|---|
| | | Soybean | Corn | Velvetleaf | Black nightshade | Common lambsquarters | Redroot pigweed |
| 1 | 5 | 1 | 1 | 5 | 5 | 5 | 5 |
| | 2.5 | 0 | 0 | 5 | 2 | 5 | 5 |
| 4 | 5 | — | — | 5 | 5 | 5 | 5 |
| | 2.5 | 0 | 0 | 5 | 5 | 5 | 5 |
| 5 | 5 | — | 1 | 5 | 5 | 5 | 5 |
| | 2.5 | 0 | 0 | 5 | 3 | 5 | 5 |
| 6 | 5 | — | 1 | 5 | 5 | 5 | 5 |
| | 2.5 | 1 | 1 | 5 | 5 | 5 | 5 |
| 7 | 5 | 0 | 0 | 5 | 4 | 5 | 5 |
| | 2.5 | 0 | 0 | 5 | 2 | 4 | 4 |
| B | 5 | 0 | 0 | 1 | 1 | 1 | 1 |
| | 2.5 | 0 | 0 | 0 | 0 | 0 | 0 |

TEST EXAMPLE 5

Vats (33 cm × 23 cm × 11 cm) were filled with upland field soil, and the seeds of soybean, velvetleaf, black nightshade and redroot pigweed were sowed therein and cultivated for 18 days in a greenhouse. A designed amount of the test compound formulated in an emulsifiable concentrate according to Formulation Example 2 or 5 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although growing stage of the test plants varied depending on their species. The results are shown in Table 10.

TABLE 10

| Compound No. | Dosage (g/are) | Herbicidal activity | | | |
|---|---|---|---|---|---|
| | | Soybean | Velvetleaf | Black nightshade | Redroot pigweed |
| 1 | 0.1 | 1 | 5 | 5 | 5 |
| 2 | 0.1 | 1 | 5 | 5 | 5 |
| 4 | 0.1 | 1 | 5 | 5 | 5 |
| 5 | 0.1 | 1 | 5 | 5 | 5 |
| 6 | 0.1 | 1 | 5 | 5 | 5 |
| 7 | 0.1 | 1 | 5 | 5 | 5 |
| 8 | 0.1 | 1 | 4 | 5 | 5 |
| A | 0.1 | 0 | 0 | 0 | 0 |
| B | 0.1 | 0 | 0 | 0 | 0 |

TEST EXAMPLE 6

Wagner's pots (1/5000 are) were filled with paddy field soil, and the seeds of barnyardgrass (*Echinochloa oryzicola*), broad-leaved weeds (e.g. common falsepimpernel, indian toothcup, waterwort) and statoblast of needle spikerush were sowed in 1 to 2 cm depth. Water was poured therein to make a flooded condition. Rice seedlings of the 4-leaf stage were transplanted therein and grown in a greenhouse. Five days (at that time barnyardgrass began to germinate) thereafter, a designed amount of the test compound formulated in an emulsifiable concentrate according to Formulation Example 2 or 5 and diluted with water (10 ml) was applied to the pots by perfusion, followed by addition of water thereto to make a 4 cm depth. The test plants were grown for further 20 days in the greenhouse, and the herbicidal activity was examined. Two consecutive days after the treatment, water was leaked out in an amount of 3 cm depth per day. The results are shown in Table 11.
TABLE 11
| Compound No. | Dosage (g/are) | Rice plant | Barn-yard-grass | Broad-leaved weed | Needle spikerush |
| --- | --- | --- | --- | --- | --- |
| 1 | 0.08 | 0 | 5 | 5 | 4 |
| 2 | 0.08 | 0 | 5 | 5 | — |
| 3 | 0.08 | 0 | — | 5 | 5 |
| 4 | 0.08 | 0 | 5 | 5 | 5 |
| 5 | 0.08 | 0 | 5 | 5 | 4 |
| 6 | 0.08 | 0 | 5 | 5 | 4 |
| 7 | 0.08 | 0 | 5 | 5 | 4 |
| A | 0.08 | 0 | 0 | 2 | 0 |
| B | 0.08 | 0 | 0 | 0 | 0 |
What is claimed is:
1. A compound of the formula:
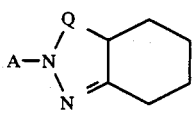
wherein A is
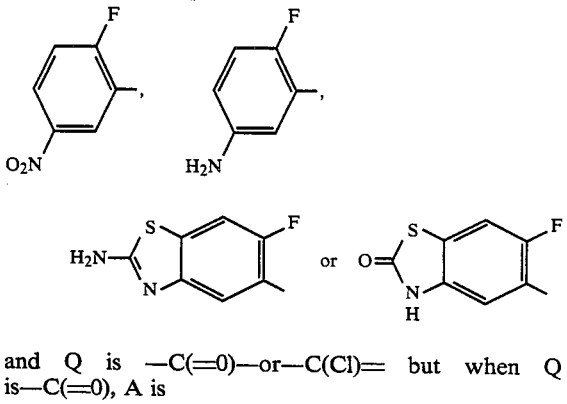
and Q is —C(=O)— or —C(Cl)= but when Q is —C(=O), A is